US012694513B2

(12) United States Patent
Schoenhagen et al.

(10) Patent No.: US 12,694,513 B2
(45) Date of Patent: *Jul. 28, 2026

(54) AUTOMATED IDENTIFICATION OF VASCULAR PATHOLOGY IN COMPUTED TOMOGRAPHY IMAGES

(71) Applicant: THE CLEVELAND CLINIC FOUNDATION, Cleveland, OH (US)

(72) Inventors: Paul Schoenhagen, Cleveland, OH (US); Po-Hao Chen, Cleveland, OH (US); Kunio Nakamura, Cleveland, OH (US); Nancy Obuchowski, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 576 days.

This patent is subject to a terminal disclaimer.

(21) Appl. No.: 17/943,494

(22) Filed: Sep. 13, 2022

(65) Prior Publication Data

US 2023/0022472 A1 Jan. 26, 2023

Related U.S. Application Data

(63) Continuation-in-part of application No. 16/906,167, filed on Jun. 19, 2020, now Pat. No. 11,475,561.

(Continued)

(51) Int. Cl.
*G06T 7/00* (2017.01)
*A61B 6/03* (2006.01)
(Continued)

(52) U.S. Cl.
CPC ........... *G06T 7/0012* (2013.01); *A61B 6/032* (2013.01); *A61B 6/12* (2013.01); *A61B 6/469* (2013.01);
(Continued)

(58) Field of Classification Search
CPC ........... A61B 6/032; A61B 6/12; A61B 6/469; A61B 6/504; G06T 2207/10081;
(Continued)

(56) References Cited

U.S. PATENT DOCUMENTS

| | | | |
|---|---|---|---|
| 9,589,211 B2 | 3/2017 | Lay et al. | |
| 2013/0004044 A1* | 1/2013 | Ross | G06T 7/0016 |
| | | | 382/128 |

(Continued)

FOREIGN PATENT DOCUMENTS

| | | |
|---|---|---|
| CN | 108764221 A | 11/2018 |
| CN | 109035255 A | 12/2018 |
| EP | 3432215 A1 | 1/2019 |

OTHER PUBLICATIONS

Kovacs, Tamás, et al. "Automatic segmentation of the aortic dissection membrane from 3D CTA images." International Workshop on Medical Imaging and Virtual Reality. Springer, Berlin, Heidelberg, 2006.

(Continued)

*Primary Examiner* — Matthew C Bella
(74) *Attorney, Agent, or Firm* — Tarolli, Sundheim, Covell & Tummino LLP

(57) ABSTRACT

Systems and methods are provided for automated identification of vascular pathology in computed tomography images. A region of interest in a chest of a patient is imaged via a computed tomography scanner to provide an image. The region of interest includes at least one of the ascending aorta, the central pulmonary artery, the left and right pulmonary arteries, the lobar arteries extending from the left and right pulmonary arteries, the aortic arch, and the descending aorta of the patient. For each of a plurality of locations within the region of interest, a value representing a variation in radiodensity values for voxels within the location is determined from the image to provide a set of (Continued)

400

402
IMAGE A REGION OF INTEREST IN A CHEST OF A PATIENT VIA A CT SCANNER TO PROVIDE IMAGES AT A PLURALITY OF LOCATIONS

404
DETERMINE A VALUE REPRESENTING A VARIATION IN HU VALUES WITHIN THE LOCATION FROM THE IMAGE FOR EACH OF THE PLURALITY OF LOCATIONS TO PROVIDE A SET OF VARIATION VALUES

406
DETERMINE A PARAMETER REPRESENTING A LIKELIHOOD THAT THE PATIENT IS EXPERIENCING VASCULAR PATHOLOGY AT A DERIVED MODEL FROM AT LEAST THE SET OF VARIATION VALUES

408
PROVIDE THE PARAMETER REPRESENTING THE LIKELIHOOD THAT THE PATIENT IS EXPERIENCING VASCULAR PATHOLOGY TO A USER AT AN ASSOCIATED OUTPUT DEVICE variation values. At a derived model, a parameter representing vascular pathology within the patient is determined from the set of variation values and provided to a user at an associated output device.

20 Claims, 5 Drawing Sheets

Related U.S. Application Data

(60) Provisional application No. 62/863,895, filed on Jun. 20, 2019.

(51) Int. Cl.

| | |
|---|---|
| *A61B 6/12* | (2006.01) |
| *A61B 6/46* | (2024.01) |
| *G06V 10/40* | (2022.01) |
| *G16H 10/60* | (2018.01) |
| *G16H 50/20* | (2018.01) |
| *G16H 50/30* | (2018.01) |

(52) U.S. Cl.
CPC ............. *G06V 10/40* (2022.01); *G16H 10/60* (2018.01); *G16H 50/20* (2018.01); *G16H 50/30* (2018.01); *G06T 2207/10081* (2013.01); *G06T 2207/30004* (2013.01)

(58) Field of Classification Search
CPC . G06T 2207/30004; G06T 2207/30101; G06T 7/0012; G06V 10/40; G06V 10/82; G06V 2201/03; G06V 40/14; G16H 10/60; G16H 30/40; G16H 50/20; G16H 50/30; G16H 50/50; G16H 50/70
See application file for complete search history.

(56) References Cited

U.S. PATENT DOCUMENTS

| | | | | |
|---|---|---|---|---|
| 2017/0265832 | A1* | 9/2017 | Antoniades ............ | G16H 50/30 |
| 2018/0263697 | A1* | 9/2018 | Eskesen ................. | G16H 30/40 |
| 2020/0334825 | A1* | 10/2020 | Gooding ................ | G16H 30/40 |
| 2021/0012226 | A1* | 1/2021 | Shi ....................... | G06V 10/764 |
| 2022/0061790 | A1* | 3/2022 | Antoniades ............ | G16H 30/40 |

OTHER PUBLICATIONS

Lopez-Linares, Karen, et al. "Fully automatic detection and segmentation of abdominal aortic thrombus in post-operative CTA images using deep convolutional neural networks." Medical image analysis 46 (2018): 202-214.

Dehghan, Ehsan, Hongzhi Wang, and Tanveer Syeda-Mahmood. "Automatic detection of aortic dissection in contrast-enhanced CT." 2017 IEEE 14th International Symposium on Biomedical Imaging (ISBI 2017). IEEE, 2017.

Krissian, Karl, et al. "Semi-automatic segmentation and detection of aorta dissection wall in MDCT angiography." Medical image analysis 18.1 (2014): 83-102.

Maiora, Josu, and Manuel Graña. "Abdominal cta image analisys through active learning and decision random forests: Aplication to aaa segmentation." The 2012 international joint conference on neural networks (IJCNN). IEEE, 2012.

Hagan, Peter G., et al. "The International Registry of Acute Aortic Dissection (IRAD): new insights into an old disease." Jama 283.7 (2000): 897-903.

Bonow, Robert O., et al. Braunwald's heart disease e-book: A textbook of cardiovascular medicine. Elsevier Health Sciences, 2011.

Rogers, Adam M., et al. "Sensitivity of the aortic dissection detection risk score, a novel guideline-based tool for identification of acute aortic dissection at initial presentation: results from the international registry of acute aortic dissection." Circulation 123.20 (2011): 2213-2218.

Cowie, Martin R., Catherine E. Chronaki, and Panos Vardas. "e-Health innovation: time for engagement with the cardiology community." European heart journal 34.25 (2013): 1864-1868.

Boyd DR, Dunea MM, Flashner BA. The Illinois plan for a statewide system of trauma centers. J Trauma. Jan. 1973;13(1):24-31. doi: 10.1097/00005373-197301000-00005. PMID: 4687243.

Cowley RA, Hudson F, Scanlan E, Gill W, Lally RJ, Long W, Kuhn AO. An economical and proved helicopter program for transporting the emergency critically ill and injured patient in Maryland. J Trauma. Dec. 1973;13(12):1029-38. doi: 10.1097/00005373-197312000-00001. PMID: 4753485.

Harris KM, Strauss CE, Duval S, Unger BT, Kroshus TJ, Inampudi S, Cohen JD, Kapsner C, Boland LL, Eales F, Rohman E, Orlandi QG, Flavin TF, Kshettry VR, Graham KJ, Hirsch AT, Henry TD. Multidisciplinary standardized care for acute aortic dissection: design and initial outcomes of a regional care model. Circ Cardiovasc Qual Outcomes. Jul. 2010;3(4):424-30. doi: 10.1161/CIRCOUTCOMES.109.920140. PMID: 20647576.

Henry Madison JD, Menssen KM, Mooney MR, Newell MC, Pedersen WR, Poulose AK, Traverse JH, Unger BT, Wang YL, Larson DM. A regional system to provide timely access to percutaneous coronary intervention for ST-elevation myocardial infarction. Circulation. Aug. 14, 2007;116(7):721-8. doi: 10.1161/CIRCULATIONAHA.107.694141. Epub Aug. 1, 2007. PMID: 17673457.

Ting HH, Rihal CS, Gersh BJ, Haro LH, Bjerke CM, Lennon RJ, Lim CC, Bresnahan JF, Jaffe AS, Holmes DR, Bell MR. Regional systems of care to optimize timeliness of reperfusion therapy for ST-elevation myocardial infarction: the Mayo Clinic STEMI Protocol. Circulation. Aug. 14, 2007;116(7):729-36. doi: 10.1161/CIRCULATIONAHA.107.699934. Epub Aug. 1, 2007. PMID: 17673456.

Jollis JG, Roettig ML, Aluko AO, Anstrom KJ, Applegate RJ, Babb JD, Berger PB, Bohle DJ, Fletcher SM, Garvey IL, Hathaway WR, Hoekstra JW, Kelly RV, Maddox WT Jr, Shiber JR, Valeri FS, Watling BA, Wilson BH, Granger CB; Reperfusion of Acute Myocardial Infarction in North Carolina Emergency Departments (RACE) Investigators. Implementation of a statewide system for coronary reperfusion for ST-segment elevation myocardial infarction. JAMA. Nov. 28, 2007;298(20):2371-80. doi: 10.1001/jama.298.20.joc70124. Epub Nov. 4, 2007. PMID: 17982184.

Lamonte MP, Bahouth MN, Magder LS, Alcorta RL, Bass RR, Browne BJ, Floccare DJ, Gaasch WR; Emergency Medicine Network of the Maryland Brain Attack Center. A regional system of stroke care provides thrombolytic outcomes comparable with the NINDS stroke trial. Ann Emerg Med. Sep. 2009;54(3):319-27. doi: 10.1016/j.annemergmed.2008.09.022. Epub Dec. 19, 2008. PMID: 19101059.

Aggarwal B, Raymond C, Jacob J, Kralovic D, Kormos K, Holloway D, Menon V. Transfer of patients with suspected acute aortic syndrome. Am J Cardiol. Aug. 1, 2013;112(3):430-5. doi: 10.1016/j.amjcard.2013.03.049. Epub May 10, 2013. PMID: 23668639.

Raymond CE, Aggarwal B, Schoenhagen P, Kralovic DM, Kormos K, Holloway D, Menon V. Prevalence and factors associated with false positive suspicion of acute aortic syndrome: experience in a patient population transferred to a specialized aortic treatment center. Cardiovasc Diagn Ther. Dec. 2013;3(4):196-204: doi: 10.3978/j.issn.2223-3652.2013.12.06. PMID: 24400203; PMCID: PMC3878122.

Aggarwal, Bhuvnesh, et al. "Transfer metrics in patients with suspected acute aortic syndrome." Circulation: Cardiovascular Quality and Outcomes 7.5 (2014): 780-782.

Schoenhagen, Paul, Mathis Zimmermann, and Juergen Falkner. "Advanced 3-D analysis, client-server systems, and cloud computing—Integration of cardiovascular imaging data into clinical workflows of transcatheter aortic valve replacement." Cardiovascular diagnosis and therapy 3.2 (2013): 80.

Schoenhagen P, Falkner J, Piraino D. Transcatheter aortic valve repair, imaging, and electronic imaging health record. Curr Cardiol Rep. Jan. 2013;15(1):319. doi: 10.1007/s11886-012-0319-1. PMID: 23250656.

(56)　　　　　References Cited

OTHER PUBLICATIONS

Matar R, Renapurkar R, Obuchowski N, Menon V, Piraino D, Schoenhagen P. Utility of hand-held devices in diagnosis and triage of cardiovascular emergencies. Observations during implementation of a PACS-based system in an acute aortic syndrome (AAS) network. J Cardiovasc Comput Tomogr. Nov.-Dec. 2015;9(6):524-33. doi: 10.1016/j.jcct.2015.07.013. Epub Aug. 3, 2015. PMID: 26277273.

Deo RC. Machine Learning in Medicine. Circulation. Nov. 17, 2015;132(20):1920-30. doi: 10.1161/CIRCULATIONAHA.115. 001593. PMID: 26572668; PMCID: PMC5831252.

Liang, Mingzhu, et al. "Low-dose CT screening for lung cancer: computer-aided detection of missed lung cancers." Radiology 281.1 (2016): 279-288.

Singal, Amit G., et al. "Machine learning algorithms outperform conventional regression models in predicting development of hepatocellular carcinoma." The American journal of gastroenterology 108.11 (2013): 1723.

Mjolsness, Eric, and Dennis DeCoste. "Machine learning for science: state of the art and future prospects." science 293.5537 (2001): 2051-2055.

Bakkar, Nadine, et al. "Artificial intelligence in neurodegenerative disease research: use of IBM Watson to identify additional RNA-binding proteins altered in amyotrophic lateral sclerosis." Acta neuropathologica 135.2 (2018): 227-247.

Huynh, Quan L., et al. "Predictive score for 30-day readmission or death in heart failure." JAMA cardiology 1.3 (2016): 362-364.

Motwani, Manish, et al. "Machine learning for prediction of all-cause mortality in patients with suspected coronary artery disease: a 5-year multicentre prospective registry analysis." European heart journal 38.7 (2017): 500-507.

Schoenhagen, Paul, et al. "Online network of subspecially aortic disease experts: Impact of "cloud" technology on management of acute aortic emergencies." (2016): 39-42.

Schoenhagen, Paul, and Neil Mehta. "Big data, smart computer systems, and doctor-patient relationship." European heart journal 38.7 (2017): 508-510.

* cited by examiner

AUTOMATED IDENTIFICATION OF VASCULAR PATHOLOGY IN COMPUTED TOMOGRAPHY IMAGES

RELATED APPLICATIONS

This application claims priority from U.S. application Ser. No. 16/906,167, filed 19 Jun. 2020 and entitled "AUTOMATED IDENTIFICATION OF ACUTE AORTIC SYNDROMES IN COMPUTED TOMOGRAPHY IMAGES," which in turn claims priority from U.S. Provisional Application No. 62/863,895, filed 20 Jun. 2019. The subject matter of each of these applications is incorporated herein by reference in its entirety.

TECHNICAL FIELD

This invention relates to diagnostic imaging, and more specifically, to automated identification of vascular pathology in computed tomography images.

BACKGROUND

The aorta is the main arterial blood vessel transporting the oxygenated blood from the lung through the left heart pumping chamber to the different organ systems including the brain, the heart muscle, the visceral organs, and the limbs. The aorta measures about three centimeters in diameter, with blood flowing in the lumen. The lumen is contained by the aortic wall, which has several layers, including, in order from the lumen to outer aspect of wall, the intima, the media, and the adventitia. Acute aortic syndromes (AAS) occur with an incidence estimated at five to thirty per one million people per year, amounting to about 10,000 cases per year in the United States. Examples of AAS include class I and class II aortic dissections as well as penetrating aortic ulcers. AAS has a high early mortality with the death rate in acute dissection as high as one percent per hour during the first twenty-four hours. Therefore prompt diagnosis and emergency treatment are critical.

Aortic dissection is defined by acute separation of the layers of the aortic wall, with the blood stream entering the aortic wall, creating a 'false lumen' within the wall, typically in the media. The remaining wall layers separating the true and false lumen are called the dissection flap. In communicating, or class I, dissections, there is blood flow in the true and false lumen, separated by a dissection flap. In contrast, in intramural hematomas, or class II dissections, the blood in the false lumen is stagnant or thrombosed.

Triage of patients with suspected AAS requires definitive imaging, and contrast enhanced computed tomography (CT) is the most common diagnostic test, with very high diagnostic accuracy. Imaging of aortic dissection with computed tomography (CT) is typically performed after iodine-based contrast injection into the blood stream, generally via an arm vein. Blood enhanced with contrast is brighter than unenhanced blood on the CT image due to increased radiodensity. Radiodensity is generally defined by Hounsfield Units (HU). Bright, contrast-enhanced blood has a Hounsfield unit of about 350 HU, while unenhanced blood has a HU of about 30 units. In communicating dissections, the contrast enhances the flowing blood in the true and false lumen, and therefore the dissection flap between the true and false lumen is visible. In most cases, the density of enhancement is different between the true and false lumen, reflecting how vigorously blood enters the false lumen, but also the timing of contrast injection. In contrast, in intramural hematomas, the false lumen does not enhance with contrast, because there is no blood flow in the false lumen. Therefore the dissection flap, which has similar HU than the thrombosed false lumen, is not visible.

Once an acute aortic syndrome is identified, further management is addressed in multidisciplinary treatment teams. Many patients with acute aortic dissection are therefore transferred to a tertiary care center with a staff experienced in managing aortic dissection and its complications. Within large healthcare systems, regional treatment networks have been established to coordinate diagnosis, triage, and treatment between initial point of contact (e.g., a local emergency room) and central specialized centers experienced in definitive pharmacologic, interventional, or surgical treatment. In these networks, a group of specialists remotely directs the initial diagnosis and triage of patients in a larger geographic area.

As described above, imaging has a critical role in the early assessment. Computed tomography is typically performed and interpreted at the initial point of access, which could include a variety of environments including the local emergency department, out-patient imaging centers, or inpatient imaging centers. While knowledge about AAS is universally high, false positive and negative reports and delayed reporting are a reality. In an investigation of the prevalence and etiology of false positive diagnoses in patients transferred to a tertiary referral center for suspected AAS, our group found false positive suspicion of dissection in seventeen of one hundred fifty (11.3%) consecutive patients transferred for suspected AAS from community emergency departments directly to the cardiac intensive care unit. False-positive activation was driven primarily by uncertainty secondary to motion artifact of the ascending aorta and the presence of complex anatomy after previous aortic intervention.

Similarly, pulmonary embolism is a blockage of an artery in the lungs by a substance that has moved from elsewhere in the body through the bloodstream, generally a blood clot. Symptoms of a pulmonary embolism may include shortness of breath, chest pain particularly upon breathing in, and coughing up blood. Severe cases can lead to passing out, abnormally low blood pressure, obstructive shock, and sudden death, and rapid administration of therapy is necessary in such cases to prevent adverse outcomes. The presence of a pulmonary embolism can be verified via chest CT angiography.

Unfortunately, interpretation of chest CT angiography requires a turnaround time of minutes to tens of minutes even under the best of circumstances, due to the time necessary for scanner equipment to process CT images and upload them to a server, the time for a technologist to verify the image quality, and the time necessary for the radiologist to review the image. Further, specifically during 'on-call' hours, the imaging specialist may not be in immediate vicinity of a workstation, further delaying interpretation of the CT image.

SUMMARY

In accordance with one aspect of the invention, a method is provided. A region of interest in a chest of a patient is imaged via a computed tomography (CT) scanner to provide an image. The region of interest includes at least one of a central pulmonary artery, a left pulmonary artery, a right pulmonary artery, lobar arteries extending from the left and right pulmonary arteries, an ascending aorta, an aortic arch, and a descending aorta of the patient. For each of a plurality of locations within the region of interest, a value representing a variation in radiodensity values for voxels within the location is determined from the image to provide a set of variation values. At a derived model, a parameter representing vascular pathology within the patient is determined from the set of variation values. The parameter representing vascular pathology is provided to a user at an associated output device.

In accordance with another aspect of the invention, a system includes a processor and a non-transitory computer readable medium storing executable instructions executable by the processor. The executable instructions, when executed provide a scanner interface that receives a computed tomography (CT) image of a region of interest in a chest of a patient from a CT scanner. The region of interest includes at least one of a central pulmonary artery, a left pulmonary artery, a right pulmonary artery, lobar arteries extending from the left and right pulmonary arteries, an ascending aorta, an aortic arch, and a descending aorta of the patient. A feature extractor determines, for each of a plurality of locations within the region of interest, a value representing a variation in radiodensity values for voxels within the location from the CT image to provide a set of variation values. A derived model determines, from at least the set of variation values, a parameter representing a likelihood that the patient is experiencing vascular pathology. A user interface provides the parameter presenting the likelihood that the patient is experiencing vascular pathology to an associated output device.

In accordance with yet another aspect of the invention, a method includes imaging a region of interest in a chest of a patient via a computed tomography (CT) scanner to provide an image. The region of interest includes at least one of the ascending aorta, the aortic arch, and the descending aorta of the patient. For each of a plurality of locations within the region of interest, a value representing a variation in radiodensity values for voxels within the location is determined from the image to provide a set of variation values. At a derived model, a parameter representing a likelihood that the patient is experiencing acute aortic syndrome is determined from the set of variation values. The parameter representing the likelihood that the patient is experiencing acute aortic syndrome is provided to a user at an associated output device.

DETAILED DESCRIPTION

Figures 1, 2:
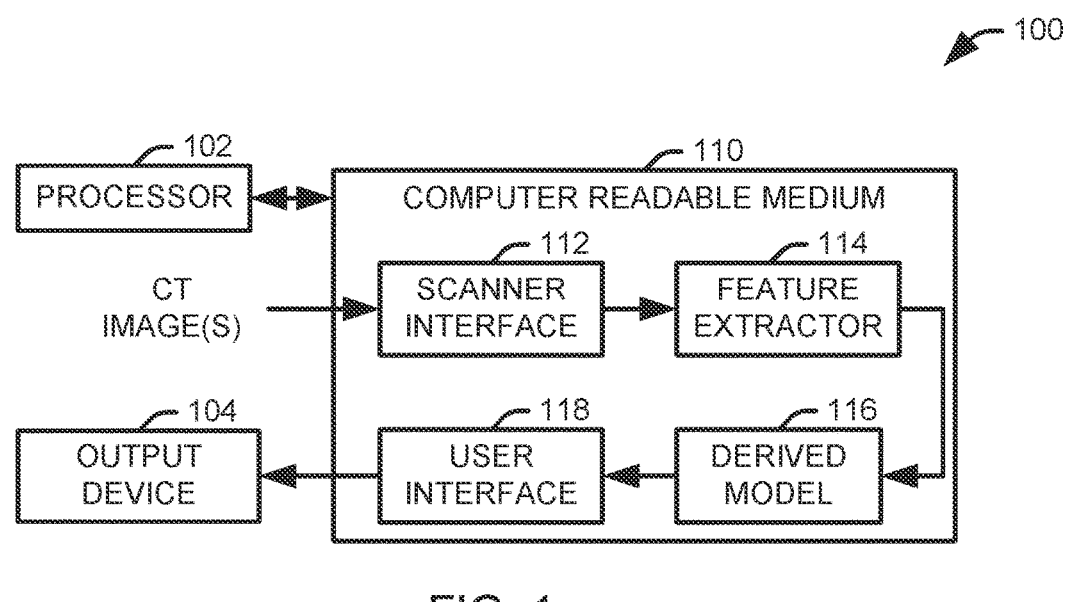
FIG. 1 illustrates an example of a system for automated identification of acute aortic syndromes in computed tomography images.
FIG. 2 illustrates an example of a system for automated identification of acute aortic syndromes in computed tomography images.

"Vascular pathology," as used herein, refers to any disorder affecting human or mammalian vasculature, and explicitly includes both pulmonary embolism and acute aortic syndrome.

An "acute vascular pathology," as used herein, refers to any disorder affecting human or mammalian vasculature that has a significant risk of an adverse outcome for the patient.

An "average," as used herein, can be any measure of central tendency, including but not limited to, an arithmetic mean, a geometric mean, a median, and a mode. It will be appreciated that, where a mean for a set of values is used as the average, the mean can be taken from a subset of the set of values to eliminate outliers within the set of values. For example, values between the fifth and the ninety-fifth percentile can be used to generate the mean.

"Spatial augmentation," as described herein refers to a linear transform or non-linear warping applied to an image.

A "value representing a variation," as used herein, can be any statistical measure of dispersion for a set of values, including but not limited to, a standard deviation, a mean absolute variation, a variance, an interquartile range, a range, a coefficient of variation, and a difference between values representing any two selected percentiles of the data set.

A "clinical parameter," as used herein, is any continuous or categorical parameter that is relevant to clinical diagnosis of a patient. Clinical parameters can include, but are not limited to, parameters representing a medical history of the patient, characteristics of the patient, such as sex and age, clinical measurements, such as aortic diameter, and current or past values for the biometric parameters of the patient, such as blood pressure, weight, body temperature, and similar values.

A "known clinical outcome," as used herein, is a determination, by a medical professional, of the presence or absence of a vascular pathology generally and/or the presence or absence of a specific type, class, or location of a vascular pathology.

A "derived model," as used herein, is a model that uses a statistical aggregation of data from patients having known clinical outcomes to predict an unknown outcome for a patient from one or more values extracted from one or more CT images of the patient.

The "ascending aorta" is defined as a region between the sinotubular junction and the proximal aortic arch.

A "radiodensity value," as used herein, includes any metric of radiodensity or radiolucency obtained from a medical image.

Systems and methods are provided herein for automated identification of vascular pathology, in particular pulmonary embolisms and acute aortic syndromes, in computed tomography (CT) images. The disclosed systems and methods extract data representing radiodensity values, such as Hounsfield Unit (HU) values, in CT images of a patient and utilize derived models to provide an immediate identification of pulmonary embolism or acute aortic syndrome without the need for expert intervention, allowing for rapid intervention. For example, the automated determination can be used to initiate surgical or pharmacological intervention, begin transfer of patients indicated to have vascular pathology to specialized treatment centers, or prioritize review of the CT imaging for the radiologist.

FIG. 1 illustrates an example of a system 100 for automated identification of vascular pathology in computed tomography images. The system 100 includes a processor 102, an output device 104, and a non-transitory computer readable medium 110 storing executable instructions executable by the processor. The executable instructions stored at the non-transitory computer readable medium 110 include a scanner interface 112 that receives CT images of a region of interest in a chest of a patient from a computed tomography (CT) scanner, either directly or by retrieving previously acquired images from a local or remote non-transitory memory. The region of interest can include one or more of the central pulmonary artery, the left and right pulmonary arteries, the lobar arteries extending from the left and right pulmonary arteries, the ascending aorta, the aortic arch, and the descending aorta of the patient. It will be appreciated that the scanner interface 112 can receive the CT images via a direct connection with the CT imager, for example, via parallel or serial bus connection, or via a network connection. In one example, the scanner interface 112 can retrieve the images from a physical or cloud server via the network connection. In some implementations, the system 100 can be integral with the CT scanner, and the scanner interface 112 can simply include instructions for conditioning a captured CT image for further analysis.

A feature extractor 114 determines a value representing a variation in radiodensity values within each of a plurality of locations within the region of interest to provide a set of variation values. For example, the plurality of locations can be represented as a set of volumes or cross-sectional planes within one or more of the central pulmonary artery, the left and right pulmonary arteries, the lobar arteries extending from the left and right pulmonary arteries, the ascending aorta, the aortic arch, and the descending aorta of the patient. In one implementation, the feature extractor 114 can determine, for each location, a plurality of representative values and determine a statistical measure of dispersion, such as the range or standard deviation, across the plurality of values. In one example, each location is divided into a plurality of regions, and a representative value is extracted from each region, for example, as a measure of central tendency for all or a portion of the region. For example, a subregion lying entirely within each region can be defined and an average value for the subregion can be used as the representative value. In one example, the subregions can be spherical subregions within a cubic volume or a rectangular prism.

In one implementation, the feature extractor 114 can be configured to evaluate each location for suitability for the analysis. In particular, a representative value representing the noise level of each location can be determined and compared to a threshold to determine if the location should be included in the analysis. In one example, a noise level is determined for each of a plurality of subregions within the location from the radiodensity values for voxels within the location, and a representative value for the noise levels associated with the plurality of subregions is calculated. The value representing the variation in radiodensity values for voxels within the location can be omitted from the analysis of the image if the representative value fails to meet a threshold value. Accordingly, high noise locations within the region of interest can be omitted from the results. If a sufficient number of the locations are found to be unsuitable, such that the number of values in the set of variation values drops below a threshold value, the feature extractor 114 can reject the entire image and instruct the scanner interface 112 to acquire another image of the patient.

The derived model 116 determines, from at least the set of variation values, a parameter representing vascular pathology in the patient. It will be appreciated that the parameter can be categorical, for example representing a presence, location, type, or class of vascular pathology, a progression of vascular pathology, a presence of acute vascular pathology, or a range of likelihoods that the patient is experiencing vascular pathology in one of those categories. The parameter can also be continuous, for example, representing the likelihood that the patient has vascular pathology generally, a specific location, type, or class of vascular pathology, or a degree of progression. In one example, the derived model 116 is a random forest model in that can determine at least the presence of vascular pathology from the set of variation values, and, in some examples, one or more of the location, type, and class of the vascular pathology.

It will be appreciated that the derived model can be trained on a plurality of training samples, each containing a set of variation values and an outcome for the patient, represented as parameter indicating if the patient experienced vascular pathology. The plurality of training samples can also be augmented via image manipulation applied to the CT image to provide additional training samples for each patient, such that the plurality of training samples including a first training sample that includes a first set of variation values derived from a first CT image associated with a subject and a parameter representing whether the subject experienced vascular pathology and a second training sample comprising a second set of variation values generated from a second CT image generated by applying an image manipulation to the first CT image and the parameter representing whether the subject experienced vascular pathology. In one example, the image manipulations include a spatial augmentation of the first CT to represent a variation in the anatomic location of a structure within the region of interest, such as the central pulmonary artery, the left and right pulmonary arteries, the lobar arteries extending from the left and right pulmonary arteries, the ascending aorta, the aortic arch, and the descending aorta of the patient.

Additionally or alternatively, the image manipulations can include an intensity augmentation of the first CT to represent a variation in the contrast enhancement of the first CT image. Still further, the image manipulations can include a variation in the diameter of one of the central pulmonary artery, the left pulmonary artery, the right pulmonary artery, the lobar arteries extending from the left and right pulmonary arteries, the ascending aorta, the aortic arch, and the descending aorta of the patient, for example, to represent the presence of an aneurysm or pulmonary hypertension. In this instance, the parameter representing vascular pathology for the patient could be changed to represent the presence of the simulated aneurysm. The output of the derived model 116 can be provided to a user interface 118 that provides the parameter presenting the likelihood that the patient is experiencing vascular pathology to the output device 104.

FIG. 2 illustrates an example of a system 200 for automated identification of acute aortic syndromes in computed tomography images. The system 200 includes a computed tomography (CT) scanner 202, a processor 204, a display 206, and a non-transitory computer readable medium 210 storing executable instructions executable by the processor. The executable instructions stored at the non-transitory computer readable medium 210 include a scanner interface 212 that receives CT images of a region of interest in a chest of a patient from a computed tomography (CT) scanner, either directly or from a non-transitory medium storing images previously acquired at the CT scanner. It will be appreciated that the scanner interface 212 can provide image preprocessing to the image. In one example, the scanner interface 212 applies a filter, having a filter kernel, to the image that replaces the value for each pixel with an average of the values within a window defined by the filter kernel.

A feature extractor 214 determines a value representing a variation in Hounsfield Unit (HU) values within each of a plurality of locations within the region of interest to provide a set of variation values. The plurality of locations can be selected as a set of volumes within one or more of the ascending aorta, the aortic arch, and the descending aorta. In the illustrated implementation, a first volume of the set of volumes is selected to fall within the ascending aorta, a second volume of each of the set of volumes is selected to coincide with a point that is above the first volume, and a third volume of each of the set of volumes is selected to coincide with a point that is below the first volume. In another implementation, the set of volumes can include between twenty and fifty volumes distributed through the ascending aorta, the aortic arch, and the descending aorta. In this example, the volumes are selected to be between one-half of a centimeter and two centimeters apart.

In the illustrated implementation, the feature extractor 214 can evaluate each volume to determine if a noise level of the image around the volume is too high to allow for effective analysis of the volume. In this implementation, the feature extractor 214 determines a noise value for each of a plurality of subregions within the volume from the radiodensity values for voxels within the volume, and a representative value for the noise levels associated with the plurality of subregions is calculated. In one example, the subregions are spherical subregions within a cubic volume, and the representative value is calculated as an average of the noise levels for the plurality of subregions. If the representative value fails to meet a threshold value, the volume can be omitted from the analysis of the image. If a sufficient number of the volumes are found to be unsuitable, such that the number of values in the set of variation values drops below a threshold value, the feature extractor 214 can reject the entire image and instruct the scanner interface 212 to acquire another image of the patient The feature extractor 214 determines, for each location, a plurality of representative values and determine a statistical measure of dispersion, such as the range or standard deviation, across the plurality of values. In one example, each location is divided into a plurality of regions, and a representative value is extracted from each region, for example, as an average for all or a portion of the region. For example, a subregion lying entirely within each region can be defined and an average value for the subregion can be used as the representative value. In the illustrated implementation, the range of the plurality of representative HU values is used, calculated as the maximum variation between any two of the representative values. In one example, the feature extractor 214 can segment the image, for example, by providing the image to a neural network 215, for example, a convolutional neural network, to generate a segmented representation of the image containing the region of interest, and determine either of a radius and a diameter of the aorta for at least one location within the aorta from the segmented representation of the image as an additional feature or features.

A machine learning model 216 determines, from at least the set of variation values, a parameter representing a likelihood that the patient is experiencing an acute aortic syndrome (AAS). It will be appreciated that the parameter can be continuous, expressed as a likelihood that the patient has an AAS, a progression of AAS, the likelihood that the patient has an AAS in a specific location (e.g., an AAS related to changes in the ascending aorta), a specific type (e.g., penetrating aortic ulcer or aortic dissection), or specific class of AAS (e.g., class II aortic dissection). The parameter can also be categorical, for example, representing ranges of likelihoods of an AAS generally or a specific type, class, or location of AAS, a degree of progression of AAS, or the likely presence of an AAS generally or a specific type, class, or location of AAS. In one example, three classes can be output, including a first class representing the likely presence of AAS, a second class representing the likely presence of a vascular pathology, such as an aneurysm, in the absence of AAS, and a third class representing no diagnosis. The output of the machine learning model is then provided to the user at the display 220 via a user interface 220.

The machine learning model can also utilize clinical parameters extracted from user data 218 stored either locally or at a remote server (not shown), including, for example, age, sex, genomic data, aortic diameter, family history, blood pressure, nutritional information, medication intake, and relevant medical history. Relevant medical conditions can include, but are not limited to, pregnancy, a history of atherosclerosis, a history of aortic aneurysm, a bicuspid aortic valve, aortic coarctation, and genetic conditions such as Turner's Syndrome, Marfan's Syndrome, other connective tissue disorders, and various inflammatory or infectious conditions.

The machine learning model 216 can utilize one or more pattern recognition algorithms, each of which analyze the extracted features or a subset of the extracted features to assign a continuous or categorical parameter to the user. Where multiple classification or regression models are used, an arbitration element can be utilized to provide a coherent result from the plurality of models. The training process of a given classifier will vary with its implementation, but training generally involves a statistical aggregation of training data into one or more parameters associated with the output class. The training process can be accomplished on a remote system and/or the local device, and can be achieved in a federated or non-federated fashion. For rule-based models, such as decision trees, domain knowledge, for example, as provided by one or more human experts, can be used in place of or to supplement training data in selecting rules for classifying a user using the extracted features. Any of a variety of techniques can be utilized for the classification algorithm, including support vector machines, regression models, self-organized maps, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

Many ANN classifiers are fully-connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used.

Figure 3:
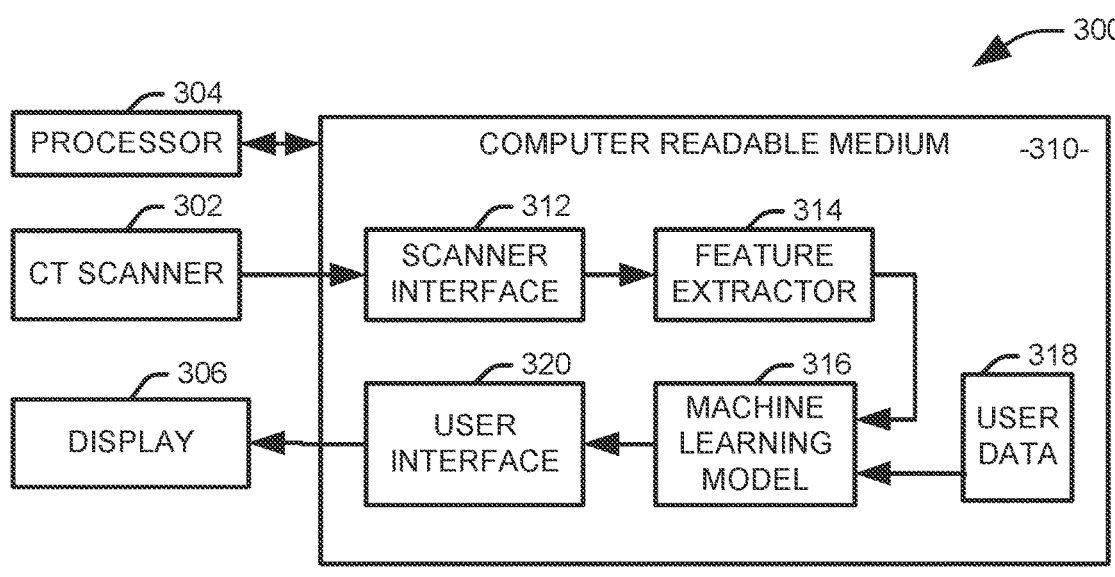
FIG. 3 illustrates an example of a system for automated identification of pulmonary embolism in computed tomography images.

FIG. 3 illustrates an example of a system 300 for automated identification of pulmonary embolisms in computed tomography images. The system 300 includes a computed tomography (CT) scanner 302, a processor 304, a display 306, and a non-transitory computer readable medium 310 storing executable instructions executable by the processor. The executable instructions stored at the non-transitory computer readable medium 310 include a scanner interface 312 that receives CT images of a region of interest in a chest of a patient from a computed tomography (CT) scanner either directly or from a non-transitory medium storing images previously acquired at the CT scanner. In one example, the scanner interface 312 applies a filter, having a filter kernel, to the image that replaces the value for each pixel with an average of the values within a window defined by the filter kernel.

A feature extractor 314 determines a value representing a variation in Hounsfield Unit (HU) values within each of a plurality of locations within the region of interest to provide a set of variation values. The plurality of locations can be selected as a set of volumes within one or more of the central pulmonary artery, the left and right pulmonary arteries, the left and right superior lobar arteries, the left and right middle lobar arteries, and the left and right inferior lobar arteries. In the illustrated implementation, a first volume of the set of volumes is selected to fall within or near the branching point of the central pulmonary artery into the left and right pulmonary arteries, a second volume of each of the set of volumes is selected to be within or near a branching point of the left pulmonary artery into the left inferior and left superior lobar arteries, and a third volume of each of the set of volumes is selected to be within or near with a branching point of the right pulmonary artery into the right inferior and right superior lobar arteries. In one example, each volume is selected to be just proximal (e.g., one millimeter proximal) of a branching point. In another implementation, the set of volumes can include between twenty and fifty volumes distributed through the central pulmonary artery and its various branches. In this example, the volumes are selected to be between one-half of a centimeter and two centimeters apart.

In the illustrated implementation, the feature extractor 314 can evaluate each volume to determine if a noise level of the image around the volume is too high to allow for effective analysis of the volume. In this implementation, the feature extractor 314 determines a noise value for each of a plurality of subregions within the volume from the radiodensity values for voxels within the volume, and a representative value for the noise levels associated with the plurality of subregions is calculated. In one example, the subregions are spherical subregions within a cubic volume, and the representative value is calculated as an average of the noise levels for the plurality of subregions. If the representative value fails to meet a threshold value, the volume can be omitted from the analysis of the image. If a sufficient number of the volumes are found to be unsuitable, such that the number of values in the set of variation values drops below a threshold value, the feature extractor 314 can reject the entire image and instruct the scanner interface 312 to acquire another image of the patient The feature extractor 314 determines, for each location, a plurality of representative values and determine a statistical measure of dispersion, such as the range or standard deviation, across the plurality of values. In one example, each location is divided into a plurality of regions, and a representative value is extracted from each region, for example, as an average for all or a portion of the region. For example, a subregion lying entirely within each region can be defined and an average value for the subregion can be used as the representative value. In the illustrated implementation, the range of the plurality of representative HU values is used, calculated as the maximum variation between any two of the representative values.

A machine learning model 316 determines, from at least the set of variation values, a parameter representing a likelihood that the patient is experiencing a pulmonary embolism. It will be appreciated that the parameter can be continuous, expressed as a likelihood that the patient has a pulmonary embolism, the likelihood that the patient has a pulmonary embolism in a specific location, or a specific type of pulmonary embolism. The parameter can also be categorical, for example, representing ranges of likelihoods of a pulmonary embolism generally or a specific type, or location of pulmonary embolism, or the likely presence of a pulmonary embolism generally or a specific type or location of pulmonary embolism. The output of the machine learning model is then provided to the user at the display 320 via a user interface 320.

The machine learning model can also utilize clinical parameters extracted from user data 318 stored either locally or at a remote server (not shown), including, for example, age, sex, genomic data, family history, blood pressure, nutritional information, medication intake, and relevant medical history. Relevant medical conditions can include, but are not limited to, obesity or a history of deep vein thrombosis, pulmonary hypertension, or other clotting disorders. It will be appreciated that the machine learning model can be implemented in a manner similar to that of the machine learning model 214 described in FIG. 2.

Figure 4:
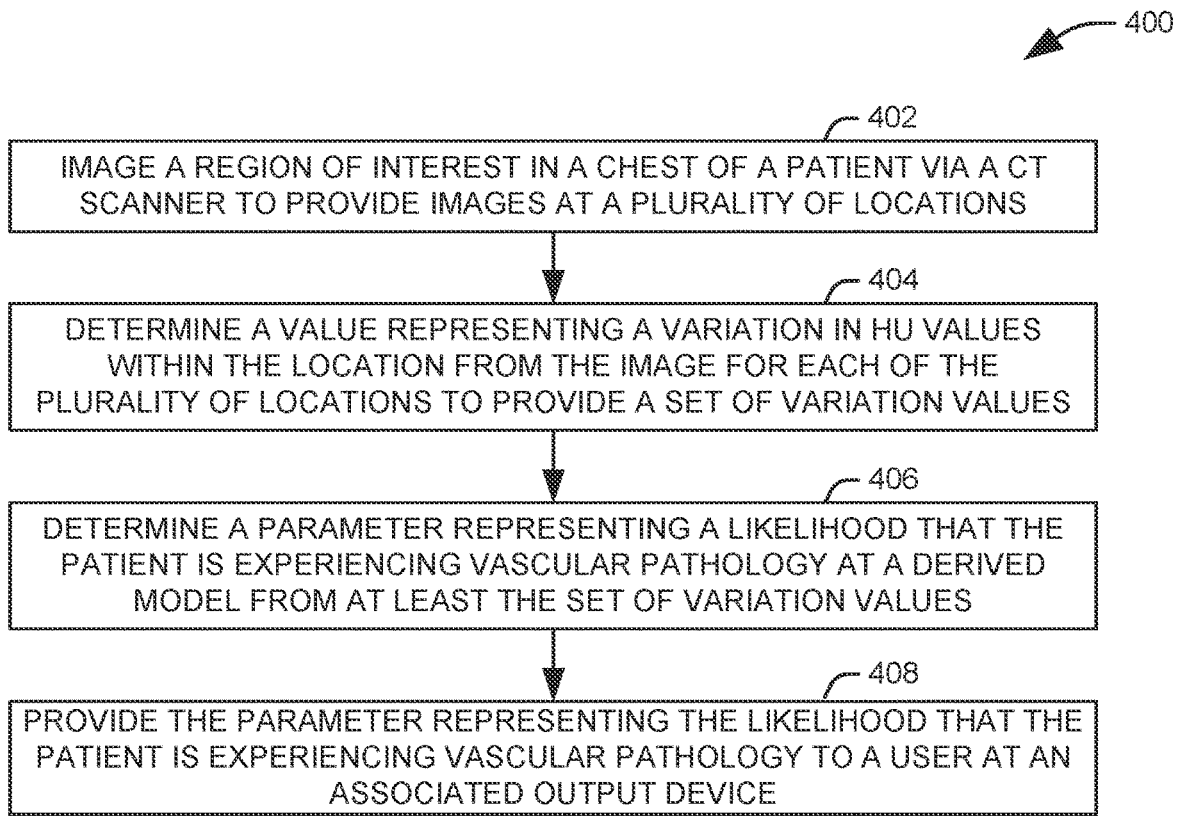
FIG. 4 illustrates one example of a method for automated identification of vascular pathology in computed tomography images.
Figure 5:
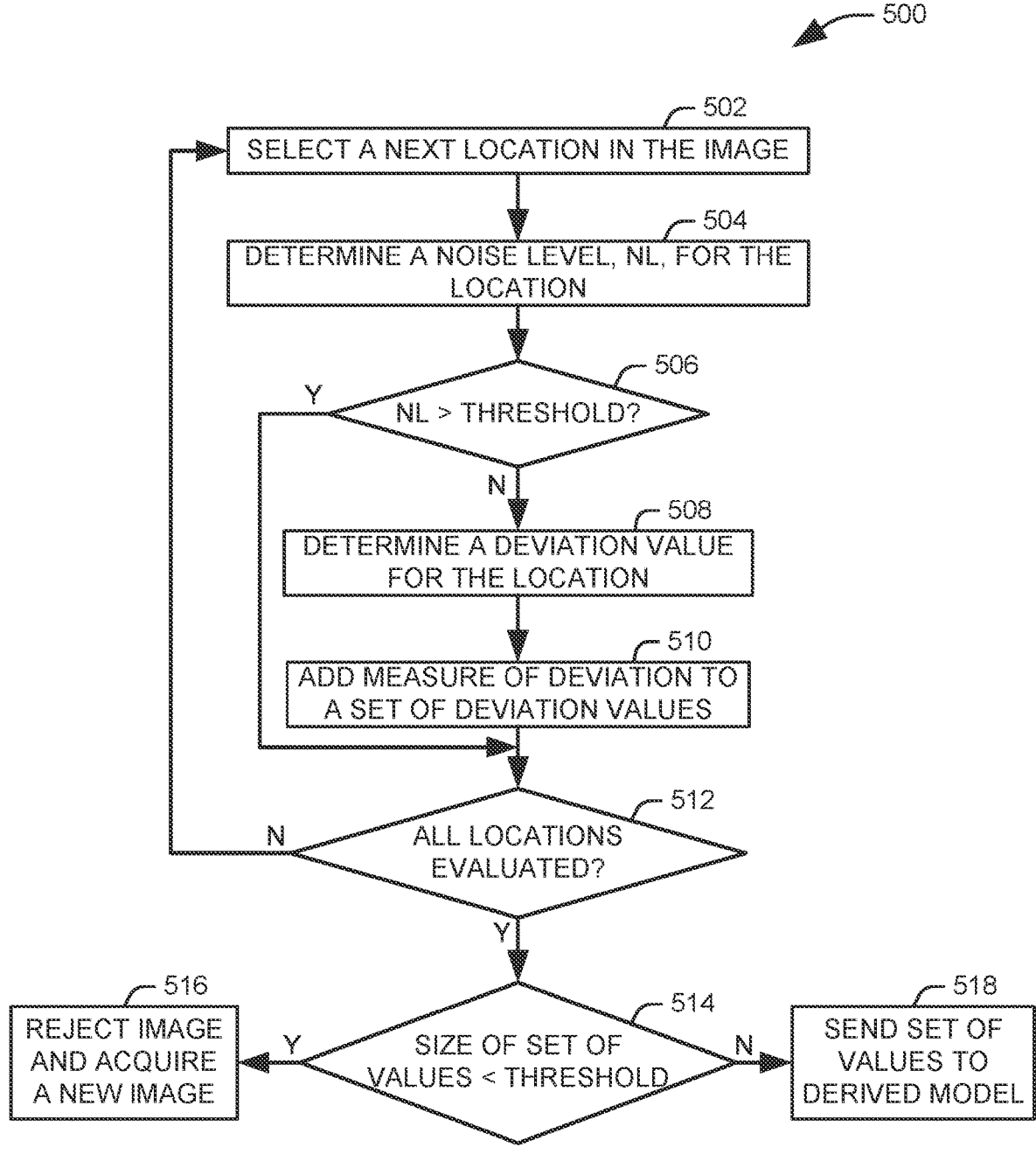
FIG. 5 illustrates one example of a method of determining a set of variation values from a computed tomography image for use in identifying vascular pathology.
Figure 6:
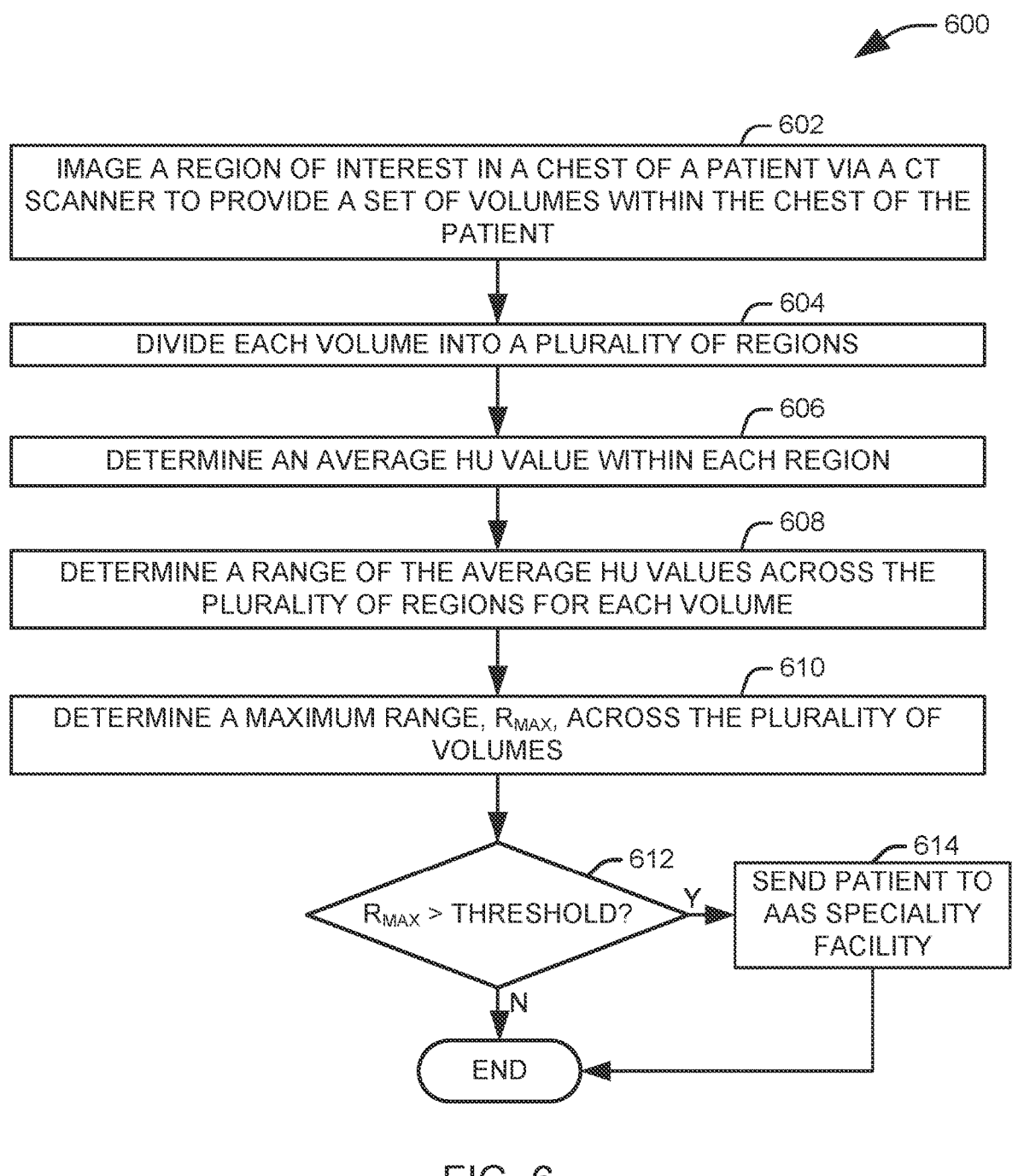
FIG. 6 illustrates one example of a method for automated identification of acute aortic syndromes in computed tomography images.

In view of the foregoing structural and functional features described above, example methods will be better appreciated with reference to FIGS. 4-6. While, for purposes of simplicity of explanation, the example methods of FIGS. 4-6 are shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method.

FIG. 4 illustrates one example of a method 400 for automated identification of vascular pathology in computed tomography images. At 402, a region of interest in a chest of a patient is imaged via a computed tomography (CT) scanner to provide images at a plurality of locations. The region of interest includes one or more of the central pulmonary artery, the left and right pulmonary arteries, the lobar arteries extending from the left and right pulmonary arteries, the ascending aorta, the aortic arch, and the descending aorta of the patient. At 404, for each of the plurality of locations within the region of interest, a value representing a variation in radiodensity values, such as Hounsfield unit (HU) values within the location is determined from the image to provide a set of variation values. In one example, the plurality of locations are defined as a set of volumes within one or more of the ascending aorta, the aortic arch, and the descending aorta. In another implementation, the plurality of locations are defined as a set of values within the central pulmonary artery and its branches.

In some implementations, the value representing a variation in radiodensity values within the location can be determined by determining a statistical measure of dispersion, such as a range, across the defined location. Alternatively, each defined location can be divided into a plurality of regions, and a representative radiodensity measurement can be obtained for each of the plurality of regions. For example, an average radiodensity value for each region can be calculated. The value representing the variation in radiodensity can be calculated from the representative radiodensity measurements for the plurality of regions. This can be done, for example, by measuring a statistical measure of dispersion across the representative values for each region. In one example, the value representing the variation in radiodensity is calculated by determining a maximum variation between any two of the representative radiodensity measurements for the plurality of regions.

FIG. 5 illustrates one example of a method 500 of determining a set of variation values from a computed tomography image for use in identifying vascular pathology. At 502, a location of the plurality of locations is selected. At 504, a noise level, NL, for the location is determined. In one implementation, the location is divided into a plurality of subregions, and a noise level for each subregion is determined. An average of the noise levels across the plurality of subregions is used as the noise level, NL, for the location. At 506, the noise level for the location is compared to a threshold value. If the noise level does not exceed the threshold value (N), the method advances to 508. At 508, a deviation value is determined for the location. In one example, the variation value is determined by determining a measure of deviation for each of the plurality of subregions and computing an average of the measures of deviation across the plurality of subregions. At 510, the deviation value for the location is added to a set of deviation values and the method advances to 512.

Returning to 506, if the noise level exceeds the threshold value (Y), the method advances directly to 512. At 512, it is determined if all of the plurality of locations have been selected. If locations remain to be selected (N), the method returns to 502 to select a new location. If all of the locations have been selected (Y), the method advances to 514, where it is determined if the size of the set of deviation values, that is, the number of values in the set of values, is less than a threshold value. If the number of deviation values in the set is less than the threshold value (Y), the image is rejected and a new image is acquired at 516. If the number of deviation values meets the threshold (N), the set of deviation values is provided to a derived model at 518.

Returning to FIG. 4 at 406, a parameter representing a likelihood that the patient is experiencing vascular pathology, such as acute aortic syndrome (AAS) or a pulmonary embolism, is determined, at a derived model from at least the set of variation values. In some implementations, the derived model can also use a set of at least one clinical parameter associated with the patient, such as age, sex, aortic diameter, blood pressure, and a parameter representing a medical history of the patient in identifying vascular pathology from CT images. The parameter can represent the presence of vascular pathology, the presence of acute vascular pathology, a progression of a vascular pathology, or a type, class, or location of vascular pathology. In one example, the parameter represents the likelihood that the patient is experiencing an acute aortic syndrome related to changes in the ascending aorta. The derived model can be any appropriate statistical or machine learning model that uses a statistical aggregation of data from patients having known clinical outcomes, and in some implementations, additional training samples generated by applying image manipulations to the CT images associated with existing samples, to predict an unknown outcome for a patient from one or more values extracted from one or more CT images of the patient. In one example, the derived model is a random forest model, and the parameter representing the likelihood that the patient is experiencing vascular pathology is a categorical parameter. At 408, the parameter representing the likelihood that the patient is experiencing vascular pathology is provided to a user at an associated output device.

FIG. 6 illustrates another example of a method 600 for automated identification of acute vascular pathology in computed tomography images. At 602, a region of interest in a chest of a patient is imaged via a computed tomography (CT) scanner to provide a set of volumes within the patient's chest, for example, in the aorta and the central pulmonary artery and its branches. At 604, each volume is divided into a plurality of regions. It will be appreciated that the regions can be of unequal size and different shapes, with the specific shapes and sizes of the regions being at least in part a function of the profile of the aorta at the selected location for the volume.

At 606, an average Hounsfield unit (HU) value across voxels is determined for each of the plurality of regions in each volume. At 608, a range across the plurality of average HU voxel values for each volume plane is determined. Effectively, the range value representing each volume is the difference between the highest average HU value for a region in the volume and the lowest average HU value for a region in the volume. A maximum range, RMAX, is selected across the plurality of volumes at 610. At 612, it is determined if the maximum range exceeds a threshold value. If so (Y), it is determined that the patient is likely to have an acute vascular pathology, and the patient is transferred to a specialty care facility at 614. Otherwise (N), it is determined that it is unlikely that the patient has an acute vascular pathology, and the method terminates.

Figure 7:
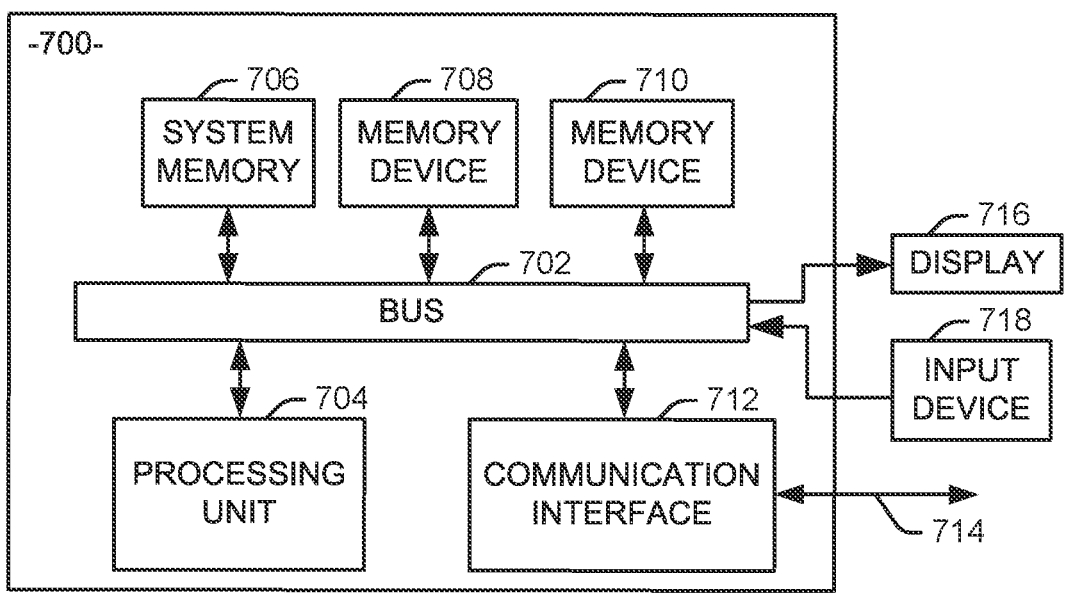
FIG. 7 is a schematic block diagram illustrating an exemplary system of hardware components that can be used to implement the systems and methods disclosed herein.

FIG. 7 is a schematic block diagram illustrating an exemplary system 700 of hardware components capable of implementing examples of the systems and methods disclosed herein. The system 700 can include various systems and subsystems. The system 700 can be a personal computer, a laptop computer, a workstation, a computer system, an appliance, an application-specific integrated circuit (ASIC), a server, a server BladeCenter, a server farm, etc.

The system 700 can include a system bus 702, a processing unit 704, a system memory 706, memory devices 708 and 710, a communication interface 712 (e.g., a network interface), a communication link 714, a display 716 (e.g., a video screen), and an input device 718 (e.g., a keyboard, touch screen, and/or a mouse). The system bus 702 can be in communication with the processing unit 704 and the system memory 706. The additional memory devices 708 and 710, such as a hard disk drive, server, standalone database, or other non-volatile memory, can also be in communication with the system bus 702. The system bus 702 interconnects the processing unit 704, the memory devices 706-710, the communication interface 712, the display 716, and the input device 718. In some examples, the system bus 702 also interconnects an additional port (not shown), such as a universal serial bus (USB) port.

The processing unit 704 can be a computing device and can include an application-specific integrated circuit (ASIC). The processing unit 704 executes a set of instructions to implement the operations of examples disclosed herein. The processing unit can include a processing core.

The additional memory devices 706, 708, and 710 can store data, programs, instructions, database queries in text or compiled form, and any other information that may be needed to operate a computer. The memories 706, 708 and 710 can be implemented as computer-readable media (integrated or removable), such as a memory card, disk drive, compact disk (CD), or server accessible over a network. In certain examples, the memories 706, 708 and 710 can comprise text, images, video, and/or audio, portions of which can be available in formats comprehensible to human beings.

Additionally or alternatively, the system 700 can access an external data source or query source through the communication interface 712, which can communicate with the system bus 702 and the communication link 714.

In operation, the system 700 can be used to implement one or more parts of a system for automated identification of vascular pathology in computed tomography images in accordance with the present invention. Computer executable logic for implementing the system resides on one or more of the system memory 706, and the memory devices 708 and 710 in accordance with certain examples. The processing unit 704 executes one or more computer executable instructions originating from the system memory 706 and the memory devices 708 and 710. The term "computer readable medium" as used herein refers to a medium that participates in providing instructions to the processing unit 704 for execution. This medium may be distributed across multiple discrete assemblies all operatively connected to a common processor or set of related processors. Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to portable or fixed storage devices, optical storage devices, wireless channels, and/or various other storage mediums capable of storing that contain or carry instruction(s) and/or data.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method comprising:
imaging a region of interest in a chest of a patient with a computed tomography (CT) scanner to provide an image, the region of interest including one of a central pulmonary artery, a left pulmonary artery, a right pulmonary artery, lobar arteries extending from the left and right pulmonary arteries, an ascending aorta, an aortic arch, and a descending aorta of the patient;
determining, for each of a plurality of locations within the region of interest, a statistical measure of dispersion of radiodensity values for voxels within the location from the image to provide a set of variation values;
determining, at a machine learning model, a parameter representing vascular pathology within the patient from the set of variation values, wherein the machine learning model is trained on a plurality of training samples, each containing a set of variation values and an outcome for the patient, represented as parameter indicating if the patient experienced vascular pathology; and
providing the parameter representing vascular pathology to a user at an associated output device.

2. The method of claim 1, further comprising, for each of the plurality of locations, performing the following:
determining a noise level for each of a plurality of subregions within the location from the radiodensity values for voxels within the location;
calculating a representative value for the noise levels associated with the plurality of subregions; and
omitting the value representing the variation in radiodensity values for voxels within the location if the representative value fails to meet a threshold value.

3. The method of claim 2, wherein the noise level for each of the plurality of subregions is calculated as a measure of deviation for the radiodensity values of voxels within the subregion.

4. The method of claim 2, wherein the representative value for the noise levels associated with the plurality of subregions is a median of the noise levels associated with the plurality of subregions.

5. The method of claim 2, wherein the image is a first image and the method further comprising rejecting the first image and generating a second image of the region of interest if a number of values in the set of variation values is below a threshold value.

6. The method of claim 1, wherein the parameter representing vascular pathology represents a likelihood that the patient is experiencing acute aortic syndrome.

7. The method of claim 1, wherein the parameter representing vascular pathology represents a likelihood that the patient is experiencing a pulmonary embolism.

8. The method of claim 1, further comprising applying a filter, having a filter kernel, to the image that replaces the value for each pixel with an average of the values within a window defined by the filter kernel.

9. The method of claim 1, further comprising:
providing the image to a neural network, the neural network generating segmented representation of the image containing the region of interest;
determining one of a radius and a diameter of the aorta for at least one location within the aorta from the segmented representation of the image; and
providing the one of the radius and the diameter of the aorta for the at least one location within the aorta to the derived model.

10. A system comprising:
a processor;
a CT scanner; and
a non-transitory computer readable medium storing executable instructions executable by the processor to provide:
a scanner interface that receives a computed tomography (CT) image of a region of interest in a chest of a patient from a CT scanner, the region of interest including one of a central pulmonary artery, a left pulmonary artery, a right pulmonary artery, lobar arteries extending from the left and right pulmonary arteries, an ascending aorta, an aortic arch, and a descending aorta of the patient;
a feature extractor that determines, for each of a plurality of locations within the region of interest, a statistical measure of dispersion of radiodensity values for voxels within the location from the CT image to provide a set of variation values;
a machine learning model that determines, from at least the set of variation values, a parameter representing a likelihood that the patient is experiencing vascular pathology, wherein the machine learning model is trained on a plurality of training samples, each containing a set of variation values and an outcome for the patient, represented as parameter indicating if the patient experienced vascular pathology; and
a user interface that provides the parameter presenting the likelihood that the patient is experiencing vascular pathology to an associated output device.

11. The system of claim 10, wherein the parameter representing a likelihood that the patient is experiencing vascular pathology comprises one of a parameter representing a likelihood that the patient is experiencing acute aortic syndrome and a parameter representing a likelihood that the patient is experiencing a pulmonary embolism.

12. The system of claim 10, wherein the feature extractor, for each of the plurality of locations, determines a noise level for each of a plurality of subregions within the location from the radiodensity values for voxels within the location, calculates a representative value for the noise levels associated with the plurality of subregions, and omits the value representing the variation in radiodensity values for voxels within the location if the representative value fails to meet a threshold value.

13. The system of claim 12, wherein the feature extractor rejects the first image and instructs the scanner interface to acquire a second image of the region of interest if a number of values in the set of variation values is below a threshold value.

14. The method of claim 1, further comprising prioritizing review of the image by a radiologist if the parameter representing vascular pathology exceeds a threshold value.

15. The method of claim 1, further comprising prioritizing treatment of the patient as part of a triage process if the parameter representing vascular pathology exceeds a threshold value.

16. The method of claim 1, further comprising transferring the patient to a facility specializing in treatment of acute aortic syndrome if the parameter representing vascular pathology exceeds a threshold value.

17. A system comprising:
a processor;
a CT scanner; and
a non-transitory computer readable medium storing executable instructions executable by the processor to provide:
a scanner interface that receives a computed tomography (CT) image of a region of interest in a chest of a patient from a CT scanner, the region of interest including one of a central pulmonary artery, a left pulmonary artery, a right pulmonary artery, lobar arteries extending from the left and right pulmonary arteries, an ascending aorta, an aortic arch, and a descending aorta of the patient;
a feature extractor that determines, for each of a plurality of locations within the region of interest, a statistical measure of dispersion of radiodensity values for voxels within the location from the CT image to provide a set of variation values;
a machine learning model that determines, from at least the set of variation values, a parameter representing a likelihood that the patient is experiencing vascular pathology, wherein the machine learning model is trained on a plurality of training samples, the plurality of training samples including a first training sample that includes a first set of variation values derived from a first CT image associated with a subject and a parameter representing whether the subject experienced vascular pathology and a second training sample comprising a second set of variation values generated from a second CT image generated by applying an image manipulation to the first CT image and the parameter representing whether the subject experienced vascular pathology; and
a user interface that provides the parameter presenting the likelihood that the patient is experiencing vascular pathology to an associated output device.

18. The system of claim 17, wherein the image manipulation comprises a spatial augmentation of the first CT to represent a variation in the anatomic location of the one of the central pulmonary artery, the left pulmonary artery, the right pulmonary artery, the lobar arteries extending from the left and right pulmonary arteries, the ascending aorta, the aortic arch, and the descending aorta of the patient.

19. The system of claim 17, wherein the image manipulation comprises an intensity augmentation of the first CT to represent a variation in the contrast enhancement of the first CT image.

20. The system of claim 17, wherein the image manipulation represents a variation in the diameter of the one of the central pulmonary artery, the left pulmonary artery, the right pulmonary artery, the lobar arteries extending from the left and right pulmonary arteries, the ascending aorta, the aortic arch, and the descending aorta of the patient.

* * * * *